United States Patent [19]

Orvik et al.

[11] Patent Number: 4,766,219

[45] Date of Patent: Aug. 23, 1988

[54] PREPARATION OF 2-CYANO-6-CHLOROPYRIDINE COMPOUNDS

[75] Inventors: Jon A. Orvik, Walnut Creek; Alexander P. Fung, Martinez; Jim Love, Walnut Creek; Thomas J. Dietsche, Berkeley, all of Calif.

[73] Assignee: The Dow Chemical Company, Midland, Mich.

[21] Appl. No.: 66,597

[22] Filed: Jun. 26, 1987

Related U.S. Application Data

[63] Continuation-in-part of Ser. No. 740,935, Jun. 3, 1985, abandoned.

[51] Int. Cl.$^4$ .................. C07D 213/57; C07D 213/85
[52] U.S. Cl. .................................. 546/286; 546/345
[58] Field of Search ........................................ 546/286

[56] References Cited

U.S. PATENT DOCUMENTS 4,367,336  1/1983  Nishiyama et al. ................. 546/286

OTHER PUBLICATIONS

Fieser & Fieser, Reagents for Organic Synthesis, vol. 7, p. 333, Wiley-Interscience Publishers, (1979).
Raphael et al., Advances in Organic Chemistry, Methods and Results, vol. 5, p. 33, Wiley-Interscience Pub. (1965).
The Merck Index, Tenth Edition, p. ONR-79, Merck & Co., Inc. Pub. 1983.

*Primary Examiner*—Alan L. Rotman
*Attorney, Agent, or Firm*—Joseph T. Majka; Ronald G. Brookens

[57] ABSTRACT

Novel methods for preparing 2-cyano-6-chloropyridines are disclosed. The compounds are useful as intermediates in preparing other intermediates or as intermediates directly used in making pesticides, especially herbicides.

18 Claims, No Drawings

PREPARATION OF 2-CYANO-6-CHLOROPYRIDINE COMPOUNDS

CROSS-REFERENCE TO RELATED APPLICATION

This is a continuation-in-part of application Ser. No. 740,935, filed June 3, 1985, now abandoned.

FIELD OF THE INVENTION

This invention relates to a method for making 2-cyano-6-chloropyridine compounds from halopyridine compounds.

BACKGROUND OF THE INVENTION

The 2-cyano-6-chloropyridine compounds are useful as intermediates in the preparation of other intermediates or as an intermediate directly used in making pesticides, especially herbicides.

Thus, it is the object of this invention to provide a method for making such compounds.

SUMMARY OF THE INVENTION

A method for preparing 2-cyano-6-chloropyridine compounds of the formula

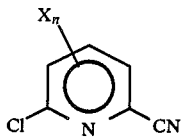

(I)

wherein X is chloro and n is an integer from 1 to 3 are prepared by contacting, in the presence of a suitable solvent, a halopyridine compound of the formula

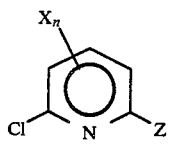

(II)

wherein X and n are defined as hereinbefore and Z is chloro, fluoro or bromo, with an effective amount of an alkali metal cyanide of the formula

MCN wherein M is an alkali metal of Group IA.

Preferred 2-cyanopyridines prepared by the present method include 2-cyanotetrachloropyridine and 2-cyano-3,6-dichloropyridine.

DETAILED DESCRIPTION OF THE INVENTION

Halopyridine compounds of Formula II utilize substituents wherein Z is chloro, fluoro or bromo, preferably chloro, most preferably fluoro.

The 2-cyano-6-chloropyridine compounds of Formula I are prepared by contacting a halopyridine compound of Formula II with an alkali metal cyanide in a molar ratio of about 1:4 (halopyridine:alkali metal cyanide), preferably in a molar ratio of about 1:0.5–1.5, most preferably about 1:1–1.5.

Alkali metal cyanides of the formula MCN, wherein M is an alkali metal of Group IA from the table of periodic elements, are well-known compounds. The alkali metal cyanides include sodium cyanide, potassium cyanide, lithium cyanide, cesium cyanide and rubidium cyanide, preferably sodium cyanide and potassium cyanide.

The halopyridine compounds may be advantageously reacted with the alkali metal cyanide at ambient pressures and at temperatures ranging from about 25° to about 130° C., preferably from about 60° to about 100° C., most preferably from about 65° to about 85° C.

The resulting reaction mixture is usually maintained, with stirring, for a period of time sufficient to provide for substantial completion of the reaction. Generally, the reaction is complete in a period from about 1 hour to about 12 hours or more.

The reaction is conducted in the presence of a solvent, such as benzonitriles, diphenyl ethers, dimethyl formamide (DMF), and N,N-dimethylacetamide (DMA), dimethylsulfone, N-methylpyrrolidinone (NMP), sulfolane and dimethyl sulfoxide (DMSO) or mixtures thereof. Preferred solvents include NMP, sulfolane and DMSO.

After the halopyridine compound has been contacted with the alkali metal cyanide, the desired 2-cyano-6-chloropyridine compound is obtained using conventional recovery procedures. In typical procedures, after the reaction has been terminated, the reaction mixture is quenched and washed with water and then extracted with organic solvents such as chlorinated hydrocarbons including chloroform, methylene chloride, carbon tetrachloride or with aromatic hydrocarbons such as xylenes or toluenes. Where desired, the reaction mixture containing the organic solvents and the aqueous washes may be filtered. After partitioning the organic phase from the aqueous phase, the organic phase may be dried over known drying agents, including sodium sulfate ($Na_2SO_4$), magnesium sulfate ($MgSO_4$) or calcium chloride ($CaCl_2$). Where desired, the 2-cyano-6-chloropyridine compounds may be further purified using conventional recovery procedures such as distillation, recrystallization and filtration.

The following examples are presented to illustrate preparation of typical compounds of the present invention, but the scope of the invention is not to be considered limited to the specific examples given.

EXAMPLE 1

Preparation of 2-cyanotetrachloropyridine from 2-fluorotetrachloropyridine and sodium cyanide A mixture of 3.3 grams (g) 2-fluorotetrachloropyridine and sodium cyanide (0.68 g) in 25 milliliters (ml) of dimethylsulfoxide (DMSO) was heated with good stirring to 70 degrees Centigrade (°C.) for 2 hours,

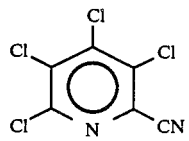

after which the temperature was raised to 100° C. for an additional 4 hours. The reaction mixture was cooled and quenched with 30 ml of ice water and extracted with 50 ml of chloroform. The organic layer was separated and dried over sodium sulfate. Analysis of the crude product by gas-liquid chromatography (GLC) and by gas-liquid mass spectroscopy (GC-MS) procedures indicated the product contained 42 percent (%) of 2-cyanotetrachloropyridine and 58 percent of 2-fluorotetrachloropyridine.

EXAMPLE 2

Preparation of 2-cyano-3,6-dichloropyridine from 2-fluoro-3,6-dichloropyridine and sodium cyanide

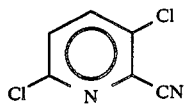

The compound 2-fluoro-3,6-dichloropyridine (16.6 g) was added to a solution containing 5.5 g sodium cyanide and 40 g dimethylsulfoxide over a period of about 20 minutes. The reaction mixture was slowly heated to 67° C. over this period, after which the mixture turned a dark brown. The temperature of the reaction mixture was lowered to 42° C. and after 4 hours was quenched by pouring the reaction mixture into 150 ml of ice water, filtered and washed. Approximately 28 g of a wet crude product having a grayish-tan color was obtained. After air drying overnight the crude product was 14.6 g, a brownish-gray solid. The yield of the crude product was 84.4 percent. Analysis of the dried product by gas-liquid chromatography (GLC) indicated the product contained 98 percent 2-cyano-3,6-dichloropyridine (melting point 92° C.) with 2.0 percent of 2-fluoro-3,6-dichloropyridine remaining.

EXAMPLE 3

Preparation of 2-cyano-3,6-dichloropyridine from 2,3,6-trichloropyridine and potassium cyanide To a solution containing 18.25 g of 2,3,6-trichloropyridine dissolved in 50 ml of NMP was added 6.5 g potassium cyanide (0.10 moles). The reaction mixture was slowly heated to 80° C. and left overnight. The mixture was removed from the heat and was diluted with water, filtered and air dried overnight to yield 13.8 g of crude grayish-brown solid containing 2-cyano-3,6-dichloropyridine.

The identity of 2-cyano-3,6-dichloropyridine in the crude product was confirmed by a combination of GC-MS, gas-liquid chromatography and mixed melting point determination. GC-MS and gas-liquid chromatography showed the crude product to be a monocyanodichloropyridine. A mixed melting point determination confirmed the location of the cyano moiety to be in the 2-position on the pyridine ring as follows:

Three grams of the crude solid were added to 16.3 g concentrated sulfuric acid and 1.6 g water. The mixture was heated to 130° C. within 1 hour and maintained at that temperature for another hour. The mixture was removed from the heat, cooled to room temperature and poured into ice water containing 50 g water and 50 g ice. The solid phase containing unreacted 2,3,6-trichloropyridine was separated from the ice water by filtration. The aqueous phase was extracted three times with methylene chloride (CH$_2$Cl$_2$). Evaporation of the methylene chloride yielded 0.6 g of 3,6-dichloro-2-picolinic acid, an off-white solid (m.p. 143°–146° C.). A mixed melting point determination of the off-white solid with a known sample of 3,6-dichloropicolinic acid confirmed the location of the carboxylic acid in the 2-position, which, in turn, confirmed the presence of the cyano precursor to have been in the 2-position. Neither 6-cyano-2,3-dichloropyridine nor 2,6-dicyano-3-chloropyridine were detected.

Preparation of Starting Materials

Pentachloropyridine, a starting material used in the preparation of the compounds of the present invention, is well known to those skilled in the art. The 2-fluoro-6-chloropyridine compounds of Formula II are prepared by reacting a 2,6-dichloropyridine compound with an alkali metal fluoride (MF) either in the presence of a suitable solvent or in the presence of a catalyst to give the requisite 2-fluoropyridine compound of Formula II. The reaction may be illustrated as follows:

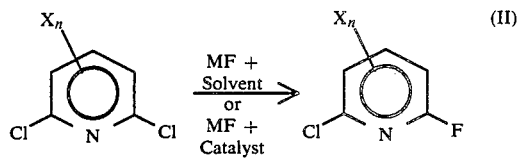

wherein X is chloride, n is an integer from 1 to 3 and M is an alkali metal of group IA.

Alkali metal fluorides are well known to one skilled in the art. Preferably, the alkali metal fluoride is sodium, most preferably potassium.

Substituted 2,6-dichloropyridine compounds used as starting materials are well known to one skilled in the art. Suitable solvents for reacting the 2-chloropyridine compound with the alkali metal include sulfolane, N-methylpyrrolidinone, DMF, DMA, dimethylsulfone, NMP and DMSO.

In preparing the 2-fluoro-6-chloropyridine compound of Formula II, the 2,6-dichloropyridine starting material is reacted with the alkali metal fluoride in a molar ratio of 1:4 (2,6-dichloropyridine:alkali metal fluoride) preferably in a molar ratio of 1:3, most preferably in a ratio of 1:1. The reaction is advantageously conducted at a temperature between about 150° to about 260° C., preferably from about 190° to about 230° C. The reaction is normally conducted at ambient pressures, but can be conducted at pressures less than ambient, such from about 50 torr to about 760 torr. The desired 2-fluoro-6-chloropyridine compound can be recovered by known recovery procedures such as distillation, recrystallization or filtration.

In an alternative method for making the 2-fluoro-6-chloropyridine compounds, the 2,6-dichloropyridine compounds is reacted with potassium fluoride in the presence of a catalyst, preferably a phase transfer catalyst. Potassium fluoride reagents and phase transfer catalyst are materials well known to those skilled in the art and include crown ethers such as 18-crown-6, dibenzo-18-crown-6, dicyclohexano-24-crown-8, and cetyltrimethylammonium bromide. The molar ratio of the starting reagents, temperatures, pressures and methods for recovery are similar to those described hereinabove.

The 2-bromo-6-chloropyridine compounds of Formula II may be prepared in a manner analogous to the methods described for the 2-fluoro-6-chloropyridine compounds.

The following examples are presented to illustrate preparation of typical compounds employed in preparing the starting materials, but the methods of preparation is not to be considered limited to the specific examples given.

EXAMPLE 4

Preparation of 2-fluorotetrachloropyridine from pentachloropyridine and potassium fluoride A 500 ml 3-necked round bottomed flask was equipped with a mechanical stirrer, a thermometer and a refluxed condenser. To the flask was added pentachloropyridine (100 g), anhydrous potassium fluoride (23.1 g), 18-crown-6 (2 g) and 350 ml of sulfolane. The reagents were mixed together with vigorous stirring at temperatures between 220° to 245° C. for 4.5 hours. The reaction mixture was then cooled and filtered. Analysis of the filtrate by gas-liquid chromatography and by GC-MS procedures indicated that the product contained 48.2 percent monofluorotetrachloropyridine, 31.2 percent difluorotrichloropyridine, 1 percent trifluorodichloropyridine and 19.6 percent unreacted pentachloropyridine. The reaction mixture was then distilled through an Oldershaw 20-tray glass column. After distilling off the lights containing the difluoro and trifluoropyridines, a fraction (9.8 g) having a boiling point of 120° C./(65 mm Hg) was collected. Analysis of this fraction by GC-MS and 19F NMR spectroscopic methods indicated the compound was 2-fluorotetrachloropyridine.

EXAMPLE 5

Preparation of 2-fluorotetrachloropyridine from pentachloropyridine and sodium fluoride To a flask equipped as described in Example 4 was added 50 g of pentachloropyridine and 30 g of sodium fluoride (molar ratio 1:3.5) and 350 ml of sulfolane. The reagents were mixed together with vigorous stirring at a temperature between 220° to 230° C. at ambient pressure for 20 hours. The reaction mixture was then cooled and filtered. Analysis of the filtrate by gas-liquid chromatography and GC-MS procedures indicated the product contained 6.2 percent 2-fluorotetrachloropyridine, 55.3 percent difluorotrifluoropyridine, 38.5 percent trifluorodichloropyridine and no unreacted pentachloropyridine.

EXAMPLE 6

Preparation of 2-fluoro-3,6-dichloropyridine from 2,3,6-trichloropyridine and potassium fluoride To a flask equipped as in Example 3 was added 91.25 g of 2,3,6-trichloropyridine (0.50 mole), 250 ml dimethylsulfoxide and 29 g of potassium fluoride (0.50 mole). The reaction mixture was heated to a temperature of 125° C. with good stirring. Analysis of a sample taken after 2.5 hours indicated the product contained 1 percent 2,6-difluoro-3-chloropyridine, 30.3 percent 2-fluoro-3,6-dichloropyridine and 68.5 percent 2,3,6-trichloropyridine. After heating the mixture overnight, a second sample taken from the reaction mixture indicated the product contained 6.5 percent 2,6-difluoro-3-chloropyridine, 66.9 percent 2-fluoro-3,6-dichloropyridine, and 26.4 percent 2,3,6-trichloropyridine. The reaction mixture was then cooled to room temperature and poured into an excess of water, extracted with methylene chloride (CH$_2$Cl) and dried on a rotary evaporator to give 78 g of a crude product. The crude product (72 g) was dissolved in methylene chloride, extracted with water to remove any dimethylsulfoxide, the solvent evaporated and product fractionally distilled to give 48 g of 2-fluoro-3,6-dichloropyridine.

What is claimed:

1. A method for preparing 2-cyano-6-chloropyridine compounds of the formula

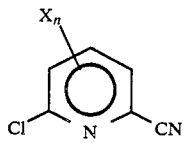

(I)

wherein X is chloro and n is an integer from 1 to 3 are prepared by contacting, in the presence of a suitable solvent, a halopyridine compound of the formula

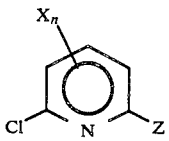

(II)

wherein X and n are defined as hereinbefore and Z is chloro, fluoro or bromo, with an effective amount of an alkali metal cyanide of the formula

MCN wherein M is an alkali metal of Group IA.

2. The method of claim 1 wherein Z is chloro.

3. The method of claim 2 wherein the 2-cyano-6-chloropyridine compound is 2-cyanotetrachloropyridine.

4. The method of claim 2 wherein the 2-cyano-6-chloropyridine is 2-cyano-3,6-dichloropyridine.

5. The method of claim 2 wherein the halopyridine compound is 2,3,6-trichloropyridine.

6. The method of claim 1 wherein Z is fluoro.

7. The method of claim 6 wherein the halopyridine compound is 2-fluorotetrachloropyridine.

8. The method of claim 6 wherein the halopyridine compound is 2-fluoro-3,6-dichloropyridine.

9. The method of claim 1 wherein Z is bromo.

10. The method of claim 1 wherein the alkali metal cyanide is sodium cyanide.

11. The method of claim 1 wherein the alkali metal cyanide is potassium cyanide.

12. The method of claim 1 wherein said contacting is performed at a temperature ranging between about 25° to about 130° C.

13. The method of claim 12 wherein the temperature is between about 60° to about 100° C.

14. The method of claim 12 wherein the temperature is between about 65° to 85° C.

15. The method of claim 1 wherein the solvent is selected from the group consisting of benzonitriles, diphenyl ethers, dimethyl formamide, N,N-dimethylacetamide, dimethylsulfone, N-methylpyrrolidinone, sulfolane, dimethyl sulfoxide and mixtures thereof.

16. The method of claim 15 wherein the solvent is N-methylpyrrolidinone.

17. The method of claim 15 wherein the solvent is sulfolane.

18. The method of claim 15 wherein the solvent is dimethylsulfoxide.

* * * * *